US012575959B2

(12) United States Patent
Powell

(10) Patent No.: US 12,575,959 B2
(45) Date of Patent: Mar. 17, 2026

(54) ANKLE SUPPORT DEVICE FOR WALKING THERAPY

(71) Applicant: Lacey Powell, Madisonville, KY (US)

(72) Inventor: Lacey Powell, Madisonville, KY (US)

( * ) Notice: Subject to any disclaimer, the term of this patent is extended or adjusted under 35 U.S.C. 154(b) by 446 days.

(21) Appl. No.: 18/075,935

(22) Filed: Dec. 6, 2022

(65) Prior Publication Data

US 2024/0180735 A1     Jun. 6, 2024

(51) Int. Cl.
*A61F 5/37*     (2006.01)
*A61F 5/01*     (2006.01)
(52) U.S. Cl.
CPC .... *A61F 5/3715* (2013.01); *A61F 2005/0197* (2013.01)
(58) Field of Classification Search
CPC ............ A61F 5/3715; A61F 2005/0197; A61F 5/0193; A61F 5/14; A61F 5/0111; A61F 5/0127; A61F 13/066; A61F 5/0102; A61F 5/0585; A61F 13/06; A61F 13/061; A63B 21/4001; A63B 21/4025
See application file for complete search history.

(56) References Cited

U.S. PATENT DOCUMENTS

| | | | | | |
|---|---|---|---|---|---|
| 2,815,021 | A | * | 12/1957 | Freeman | A61F 5/0104 |
| | | | | | 602/24 |
| 4,815,731 | A | * | 3/1989 | Suarez | A63B 21/055 |
| | | | | | 482/126 |
| 5,795,274 | A | * | 8/1998 | Kasbohm | A63B 21/00069 |
| | | | | | 482/126 |
| 5,807,218 | A | * | 9/1998 | Nagatomo | A61F 5/3715 |
| | | | | | 128/869 |
| 6,039,706 | A | * | 3/2000 | Bolla | A61F 5/05825 |
| | | | | | 602/5 |

* cited by examiner

*Primary Examiner* — Ophelia A Hawthorne
(74) *Attorney, Agent, or Firm* — Lyman Moulton, Esq.; Moulton Patents, PLLC

(57)     ABSTRACT

The Ambulatory Device is the only product of its kind that has the capability of spacing the legs and feet apart at a proper width to prevent slipping, tripping, and falling when relearning how to walk. This unprecedented device is uniquely designed with an adjustable bar that can be modified to accommodate specific user body metrics and is carefully crafted with durable, high-quality materials to ensure long-term sustainability during private or therapeutic sessions.

11 Claims, 3 Drawing Sheets

ANKLE SUPPORT DEVICE FOR WALKING THERAPY

BACKGROUND

Post severe medical conditions, such as: strokes, traumatic brain injury (TBI), or other muscular or neurological challenges, a person can find it difficult to learn how to walk again. With therapy, many patients struggle to keep their legs and feet shoulder width apart and will often step and trip on their feet resulting in them becoming unsteady and feeling insecure in their gait. There have been no products available as original equipment or as an aftermarket to address this problem.

An apparatus to help patients who have suffered severe medical conditions become steady and secure in their gait. is not being met by any known device or system at present. There have been no products available as original equipment or as an aftermarket to address this problem either.

SUMMARY OF THE INVENTION

The main purpose of the ankle support device for walking therapy is to provide users with an ankle strap that allows patients to walk normally while eliminating the potential to trip over their own feet as they regain confidence.

A walking aid device for a wearer includes a brace comprising two ends and having a length adjustable between the two ends, a swivel joint at each of the two ends, and an ankle strap for each of two ankles and each comprising an overlap outside cuff adjacent a fibula of the wearer and an inside cuff adjacent a tibia of the wearer and configured to receive the swivel joint.

Figure 1:
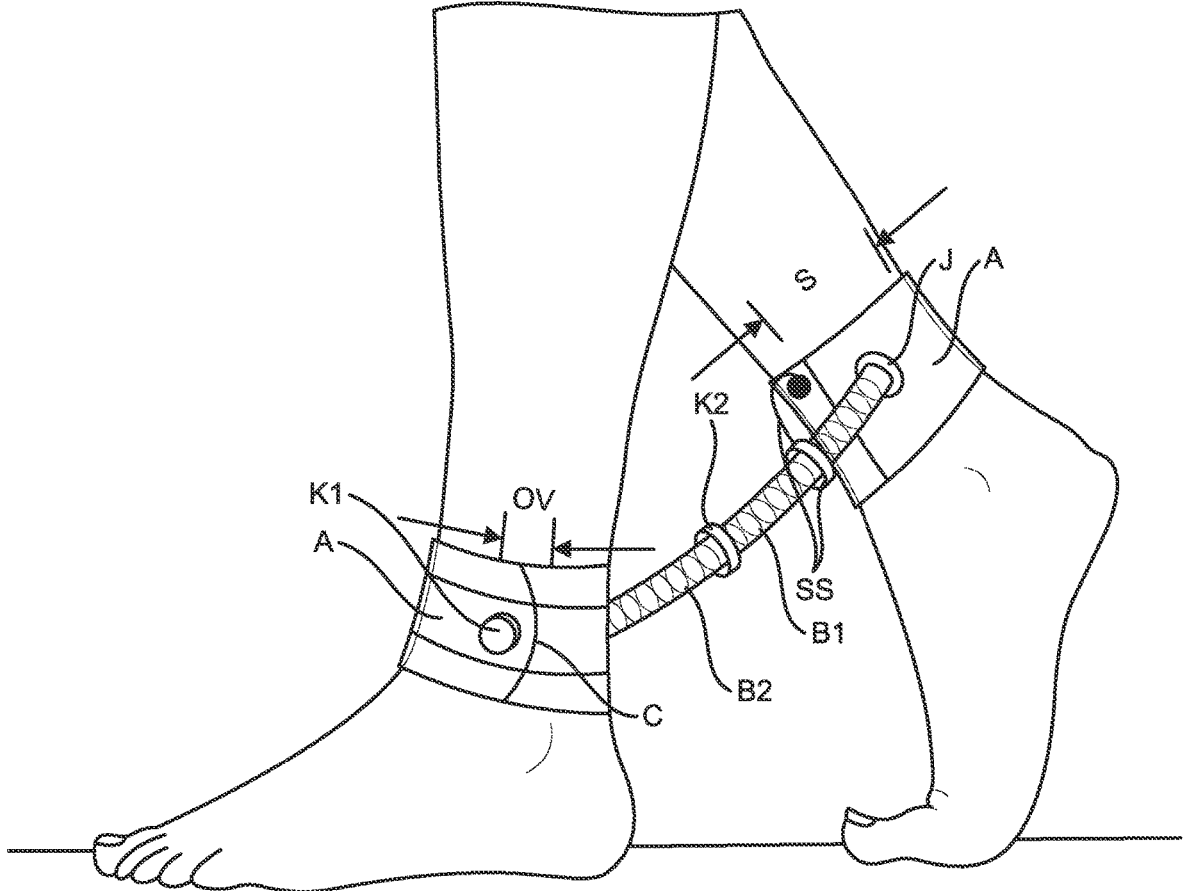
FIG. 1 is a left elevational view of the ankle support device for walking therapy in accordance with an embodiment of the present disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

FIG. 1 is a left elevational view of an ankle support device for walking therapy showing: cushioned ballistic Nylon strap referenced as A, a brace referenced as portions B1 and B2, which is a tightly coiled spring, a telescoping brace and a hard shell bungee in embodiments, a quick twist knob that allows tension of springs to be tightened or loosened referenced as K1 adjacent a fibula of a wearer and K2 concentric with the brace portions B1 and B2, in accordance with an embodiment of the present disclosure. Also depicted are the overlap OV of the cuff C for an attachment of respective ends of the cuff C, the tibia shock absorbing padding S, the swivel joint J and the safety strap SS for the event a failure of the swivel joint connection of the brace B1 and B2 portions are disreceived or disjointed into the ankle straps by material failure or by stress of operation. Two safety straps SS, one for each respective end of the brace B1 and B2 portions are also disclosed (inside tibia omitted for illustration simplicity).

The present disclosed ankle support device for walking therapy, also known as "Ambulatory Device", offers a modern accessory that provides patients a supportive device able to keep their feet at the appropriate distance in effort to re-train their musculoskeletal system to maintain a normal gait pattern. Expanding on the initial design of an average ankle strap, the Ambulatory Device introduces a novel device meant to be attached to both ankles while being connected by an adjustable rubber bar or tightly coiled spring, in between, serving to outline the consistency of keeping the legs shoulder width apart but flexible enough to allow movement, independent steps to be taken by the wearer. Within the spring section between the ankle pieces there could be an option to insert a push-button mechanism that follows the pattern of the coiled spring allowing the device to be shortened or lengthened by twisting the spring allowing the button to pop into place in multiple spots depending on desired width. This will help ensure universal use so that it can be adjusted for any height which correlates with being shoulder width apart. Once the Ambulance Device is worn, the device will help users maintain a shoulder width stance to solve the issue of having too narrow of a base of support which serves to benefit the rehab experience and accelerate a patients progression toward walking at abnormal gait again. By training individuals how to put one foot in front of the other and teaching them how to take focused steps, the device permits muscle groups of lower extremities to gain muscle memory that is required in order to learn how to consistently walk with a normal gait pattern in a safe autonomous manner. This innovative, top-quality product ensures a fully operational medical device that will benefit patients as well as doctors who seek to have a more effective and practical means of reestablishing walking patterns post-severe medical diagnoses.

Figure 2:
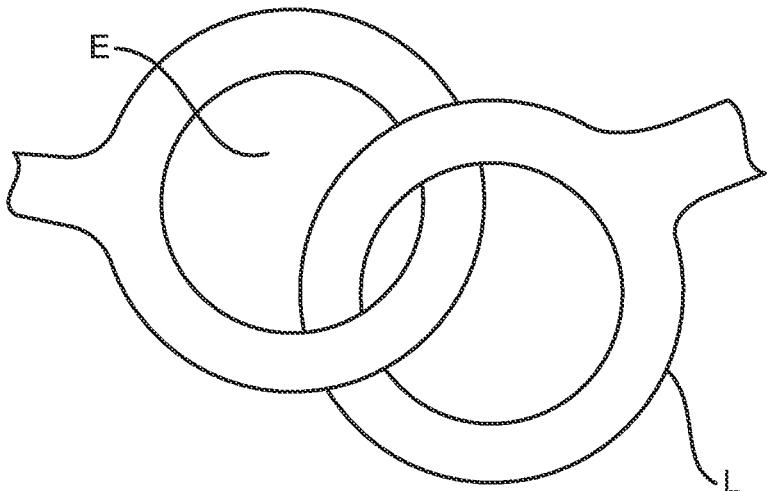
FIG. 2 depicts a crook and eye swivel joint of the brace to the ankle straps in accordance with an embodiment of the present disclosure. The crook E engages with the eyelet L to form a swivel connection.

FIG. 2 depicts a crook and eye swivel joint of the brace to the ankle straps in accordance with an embodiment of the present disclosure. The crook E engages with the eyelet L to form a swivel connection.

Figure 3:
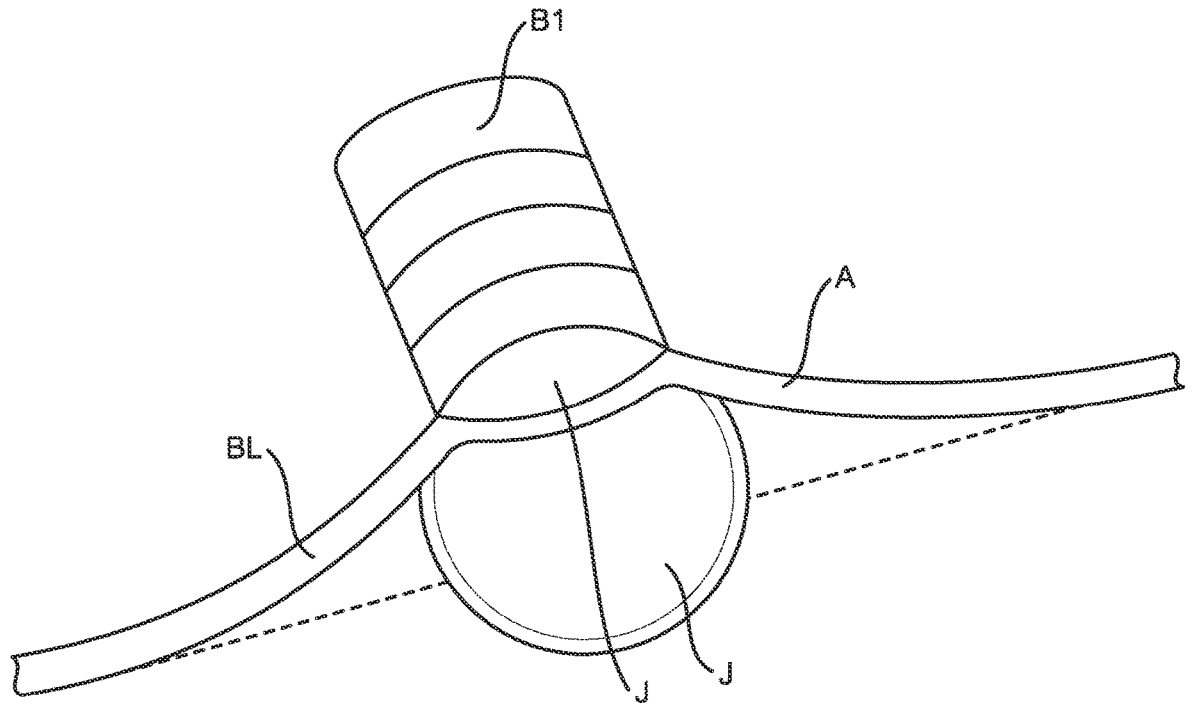
FIG. 3 depicts a ball swivel joint connection between the brace and the ankle strap boss in accordance with an embodiment of the present disclosure.

FIG. 3 depicts a ball swivel joint connection between the brace and the ankle strap boss in accordance with an embodiment of the present disclosure. The depiction includes a cross section of the ankle strap boss BL retaining or receiving the ball J connected to the brace B1 or brace B2 depending on design and engineering parameters in embodiments. The ball J therefore swivels within the boss BL to enable the brace to move in accordance with a walking motion of the wearer.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

What is claimed is:

1. A walking aid device for a wearer comprising:

a brace comprising two ends and having a length adjustable between the two ends;

a tension knob configured to adjust a tension of the brace between the two ends, wherein a first brace portion telescopes into a second brace portion via an adjustment of the tension knob;

a swivel joint connected at each of the two ends of the brace; and an ankle strap configured for each of two ankles and each ankle strap comprises an overlap outside cuff and an inside cuff configured to receive the swivel joint;

wherein the tension knob is disposed on the overlap outside cuff.

2. The walking aid device of claim 1, further comprising a safety strap connected to the brace and connected to the ankle strap as a failsafe for the swivel joint connection to the brace.

3. The walking aid device of claim 2, wherein the safety strap further comprises a first safety strap connected to one of the two ends of the brace and a second safety strap connected to another of the two ends of the brace.

4. The walking aid device of claim 1, wherein the brace comprises a tightly coiled high spring constant spring.

5. The walking aid device of claim 1, wherein the swivel joint is a ball joint.

6. The walking aid device of claim 1, wherein the tension knob is concentric with the brace.

7. The walking aid device of claim 1, wherein the ankle straps receives the swivel joint via a boss in the ankle strap.

8. The walking aid device of claim 1, wherein the overlap comprises a hook and a loop attachment and closure.

9. The walking aid device of claim 1, wherein the overlap comprises a buttoned knob and eyelet attachment and closure.

10. The walking aid device of claim 1, further comprising a shock absorbing padding adjacent the inside cuff.

11. The walking aid device of claim 1, wherein each of the ankle straps comprise ballistic nylon material.

* * * * *